(12) United States Patent
van de Voort et al.

(10) Patent No.: US 9,014,991 B2
(45) Date of Patent: Apr. 21, 2015

(54) SYSTEM AND METHOD FOR DETERMINING MOISTURE CONTENT OF HYDROPHOBIC FLUIDS

(75) Inventors: Frederik R. van de Voort, Dollard des Ormeaux (CA); David Pinchuk, Montreal West (CA)

(73) Assignee: Thermal-Lube, Inc., Point Claire (CA)

( * ) Notice: Subject to any disclaimer, the term of this patent is extended or adjusted under 35 U.S.C. 154(b) by 884 days.

(21) Appl. No.: 13/171,548

(22) Filed: Jun. 29, 2011

(65) Prior Publication Data

US 2011/0320135 A1 Dec. 29, 2011

Related U.S. Application Data

(60) Provisional application No. 61/359,551, filed on Jun. 29, 2010.

(51) Int. Cl.

| | |
|---|---|
| *C11B 3/12* | (2006.01) |
| *G01N 21/35* | (2014.01) |
| *G06F 19/00* | (2011.01) |
| *G01N 1/40* | (2006.01) |
| *G01N 21/27* | (2006.01) |
| *G01N 21/3554* | (2014.01) |
| *G01N 21/3577* | (2014.01) |
| *G01N 33/28* | (2006.01) |

(52) U.S. Cl.
CPC .............. *G01N 1/4055* (2013.01); *G06F 19/00* (2013.01); *C11B 3/12* (2013.01); *G01N 1/4005* (2013.01); *G01N 21/274* (2013.01); *G01N 21/3554* (2013.01); *G01N 21/3577* (2013.01); *G01N 33/2847* (2013.01); *G01N 2021/3595* (2013.01)

(58) Field of Classification Search
CPC .............. C11B 3/00; C11B 3/12; C11B 7/00; C11B 7/0008; G01D 7/00; G01D 9/00; G01D 21/00; G01N 221/00; G01N 21/17; G01N 21/25; G01N 21/31; G01N 21/35; G01N 21/3554; G01N 33/00; G01N 33/26; G01N 33/28; G01N 33/2835; G01N 33/2847; G06F 11/00; G06F 11/30; G06F 11/32; G06F 11/34; G06F 17/00; G06F 17/40; G06F 19/00; G06F 15/00; G06F 15/16; G06F 17/10
USPC .................. 73/1.01, 1.02, 1.03, 53.01, 61.41, 73/61.43, 61.44, 61.48, 73, 432.1, 865.8, 73/866.3; 250/252.1, 301, 336.1, 338.1, 250/339.01, 339.06, 339.1; 702/1, 22, 23, 702/25, 27, 28, 85, 127, 178, 189; 708/100, 708/105, 200
See application file for complete search history.

(56) References Cited

U.S. PATENT DOCUMENTS

| | | | | |
|---|---|---|---|---|
| 2,767,574 | A * | 10/1956 | Schurch | 73/61.43 |
| 3,770,974 | A * | 11/1973 | Fertig | 250/344 |
| 5,889,683 | A | 3/1999 | Ismail et al. | |
| 8,068,218 | B2 * | 11/2011 | Higgins et al. | 356/70 |
| 8,941,827 | B2 * | 1/2015 | Liaw et al. | 356/246 |
| 2009/0257047 | A1 * | 10/2009 | Higgins et al. | 356/51 |
| 2013/0169949 | A1 * | 7/2013 | Liaw et al. | 356/51 |
| 2015/0070702 | * | 3/2015 | Liaw et al. | 356/441 |

FOREIGN PATENT DOCUMENTS

WO    WO 2008/092180 A1 *    8/2008

OTHER PUBLICATIONS

A New Fourier Transform Infrared Method for the Determination of Moisture in Edible Oils; Ahmed Al-Alawi, Frederick R. Van De Voort, Jacqueline Sedman, applied Spectroscopy, vol. 59, No. 10, 2005, pp. 1295-1299.

An Automated FTIR Method for the Routine Quantitative Determination of Moisture in Lubricants: An Alternative to Karl Fischer Titration; Frederick R. Van De Voort, Jacqueline Sedman, Robert Cocciardi, Steve Juneau, Talanta The International Journal of Pure and Applied Analytical Chemistry, vol. 72, Issue 1, Apr. 15, 2007.

Quantitative Moisture Measurements in Lubricating Oils by FTIR Spectroscopy Combined With Solvent Extraction Approach, ENG-POH NG, Svetlana Mintova, Microchemical Journal 98 (2011) 177-185.

Automated Acid Content Determination in Lubricants by FTIR Spectroscopy as an Alternative to Acid Number Determination, D. Li et al., Journal of ASTM International, vol. 6. No. 6, May 2009.

Automated Analysis of Edible Oils and Lubricants by FTIR Spectroscopy: Problems and Solutions, F.R. Van De Voort, presented at Laboratory Automation and Practices: An Overview, Oct. 26, 2006.

Automated FTIR Analysis of Free Fatty Acids or Moisture in Edible Oils, Ahmed Al-Alawi et al., JALA, Feb. 2006, pp. 23-29.

Quantitative Determination of Moisture in Lubricants by Fourier Transform Infrared Spectroscopy, F.R. Van De Voort et al., Applied Spectroscopy, vol. 58, No. 2, 2004, pp. 193-198.

The Determination of Acid and Base Number in Lubricants by FTIR Spectroscopy. Van De Voort, F.R., Sedman, J., Yaylayan, V. and Saint-Laurent, C. Applied Spectroscopy 57(11): 1425-1431 (2003).

FTIR Acid and Base Number Analysis: Their Potential to Replace ASTM Methods. Van De Voort, F.R., Pinchuk, D., Davies, M. and Taghizadeh, A. JOAP International Condition Monitoring Conference. (2002).

New FT-IR Methods for Determining Acid Number and Base Numbers in Lubrication. Van De Voort, F.R., Saint-Laurent, C., Sedman, J. and Pinchuk, D. Lubrication and Fluid Power 3(2): 12-16 (2002).

Determination of Total Base Number (TBN) in Lubricating Oils by Mid-FTIR Spectroscopy. Dong, J., Van De Voort, F.R., Yayyalan, Y. and Ismail, A.A. (2001). Journal of the Society of Tribologists and Lubrication Engineers 3: 23-29.

Simple, Rapid and Cost Effective Determination of TAN, TBN and H2O by Differential FTIR Spectroscopy, Van De Voort, F.R. Pinchuk, D. and Pinchuk, J. Practicing Oil Analysis. Proceedings of the International Conference and Exhibit Tulsa, OK, USA, Oct. 24-26, 2000. Noria Inc. pp. 167-171.

A Novel Method to Determine TAN, TBN and Moisture Using FTIR Spectroscopy. Dong, J., Ismail, A.A. and Van De Voort, F.R. JOAP International Condition Monitoring Conference, FL. (2000).

Rapid Determination of the Carboxylic Acid Contribution to Total Acid Number of Lubricants by Fourier Transform Infrared Spectroscopy. Dong, J., Van De Voort, F.R., Ismail, A.A., Akochi-Koble, E. and Pinchuk. D. (2000). Lubrication Engineering 6:12-20.

A New Approach to the Determination of Moisture in Hydrocarbon Lubricating Oils by Mid-FTIR Spectroscopy. Dong, J., Van De Voort, F.R., Yaylayan, V. and Ismail, A.A. Journal of the Society of Tribologists and Lubrication Engineers 56(11): 30-37 (2000).

* cited by examiner

*Primary Examiner* — Edward Cosimano
(74) *Attorney, Agent, or Firm* — Gordon & Jacobson, PC (57) ABSTRACT

A system and method for quantitatively characterizing moisture content of an at least partially hydrophobic fluid sample. The method includes providing a dry solution of an aprotic solvent, adding at least a part of the fluid sample to the solvent to produce an extract-sample, performing infrared spectroscopic testing on the extract-sample to generate absorbance data representing at least one absorbance characteristic of the extracted sample, and generating moisture data for the sample based on the extracted sample data. The system includes a cell for holding and evaluating an extracted sample, an infrared spectrometer for measuring infrared absorbance characteristics of the extracted samples, a computer equipped with software for analyzing data outputted by the infrared spectrometer and utilizing an empirical model to derive at least one calibration equation relating data representing the absorbance characteristics of the extract-sample to unit moisture concentration, and converting the unit moisture concentration to a measure of moisture content of the sample. The method also utilizes $D_2O$ to characterize moisture content of the extraction solvent, and compensate for both moisture content of the extraction solvent and matrix effects stemming from miscibility of the hydrophobic fluid in the extraction solvent.

20 Claims, 7 Drawing Sheets

SYSTEM AND METHOD FOR DETERMINING MOISTURE CONTENT OF HYDROPHOBIC FLUIDS

CROSS-REFERENCE TO RELATED APPLICATIONS

The present application claims priority from expired U.S. Provisional Pat. Appl. No. 61/359,551, entitled "System and Method for Determining Moisture Content in Generally Hydrophobic Products," filed on Jun. 29, 2010, herein incorporated by reference in its entirety.

BACKGROUND OF THE INVENTION

1. Field of the Invention

This invention relates broadly to a system and method for compositional analysis of generally hydrophobic fluids (such as lubricants, edible oils, and fuels such as biodiesel). More particularly, the invention relates to systems and methods for determining the total moisture content of such fluids using infrared spectroscopy, in particular with Fourier Transform Infrared (FTIR) spectroscopy, to determine the moisture content of such hydrophobic fluids.

2. State of the Art

Infrared (IR) spectroscopy is the subset of spectroscopy that deals with the infrared region (e.g., typically including wavelengths from 0.78 to approximately 300 microns) of the electromagnetic spectrum. It covers a range of techniques, the most common being a form of absorption spectroscopy. As with all spectroscopic techniques, it can be used to identify compounds or investigate sample composition. A common laboratory instrument that uses this technique is an infrared spectrophotometer. Infrared spectroscopy exploits the fact that molecules have discrete rotational and vibrational energy levels and absorb infrared light at specific frequencies that are determined by the differences in energy between these discrete energy levels.

In IR absorption spectroscopy, the infrared spectrum of a sample is recorded by passing a beam of infrared light through the sample or placing the sample on the surface of an internal reflection element through which a beam of infrared light is passed by total internal reflection. Measurement of the transmitted or totally internally reflected light striking a detector reveals how much energy was absorbed at each wavelength. This can be done with a monochromatic beam, which changes in wavelength over time. Alternatively, a polychromatic IR beam (e.g., a range of IR wavelengths) can be passed through the sample to measure a range of wavelengths at once. From this, a transmittance or absorbance spectrum (referred to herein as a "spectrum") is produced, showing the IR wavelengths at which the sample absorbs. Analysis of the absorbance spectrum for the sample reveals details about the molecular structure of the sample.

Fourier Transform Infrared (FTIR) spectroscopy is a form of IR absorption spectroscopy that utilizes an interferometer placed between a polychromatic source of IR light and the sample. Measurement of the light striking the detector produces an interferogram. Performing a Fourier transform on the interferogram shows the IR wavelengths at which the sample absorbs. The development of FTIR technology has substantially enhanced the utility and sensitivity of IR spectroscopy as a tool for quantitative analysis. In addition, various data analysis techniques have been developed to facilitate accurate quantitative analysis of highly complex sample mixtures subjected to IR spectroscopic examination. The information inherent in the absorbance spectrum of such sample mixtures includes information at the molecular level about the chemical composition of the mixture. Thus, FTIR technology and analysis allows for the determination of the concentrations of the components in the sample mixture, and for the detection of contaminants or other unwanted chemical components or compounds in the sample mixture.

One area in which FTIR spectroscopy has been extensively utilized is in the monitoring of the condition of lubricating fluids, an activity which has commonly been performed in commercial laboratories. For example, FTIR spectroscopy has been employed to monitor the levels of additives present in such fluids and of degradation products that may be generated as a result of breakdown of the fluid. In another example, the amount of water present in lubricating oils has been quantified by means of a "splitting" method that utilizes a stoichiometric reaction between water and 2,2-dimethoxypropane (DMP) to produce acetone, a product which is readily measured by IR spectroscopy. This splitting method includes diluting an oil sample and splitting it into two parts. One of the two parts is treated with a blank reagent. The other part is treated with a reactive reagent (DMP). Both parts are then analyzed using FTIR spectroscopy, and moisture measurements are obtained by subtracting the spectrum of the sample treated with the blank reagent from the spectrum of the sample treated with the reactive reagent to eliminate the spectral features of the oil, leaving only the spectral changes related to the reaction. This FTIR method was an improvement over the ASTM Karl Fischer (KF) titration method, a methodology commonly used to measure water in oil samples. It allowed the amount of moisture in an oil sample to be quantified while avoiding the limitations of the KF method, such as its susceptibility to oil additive interferences that affect the accuracy and precision of the data obtained.

In another example described by A. Al-Alawi, F. van de Voort, and J. Sedman in "*A New Fourier Transform Infrared Method for the Determination of Moisture in Edible Oils*," Applied Spectroscopy, Vol. 59, No. 10, 2005, pgs. 1295-1299, an FTIR method for determining moisture (water) in edible oils is disclosed. The method extracts moisture from the lubricant into acetonitrile. The method employs three empirical relationships derived by calibration that translates the absorbance measured at three different wavelengths (3629 $cm^{-1}$, 3541 $cm^{-1}$, 1631 $cm^{-1}$) relative to a baseline at 2500 $cm^{-1}$ into a concentration (ppm) of moisture. Importantly, the miscibility of the oil in the acetonitrile solvent can contribute to absorbance at these wavelengths and thus reduce the accuracy of the moisture measurements derived from such methodology. Moreover, background moisture content of the acetonitrile solvent itself can contribute to absorbance at these wavelengths and thus reduce the accuracy of the moisture measurements derived from such methodology.

SUMMARY OF THE INVENTION

The present invention is directed to a system and method for generating data characterizing the moisture content (e.g., concentration of water) in a fluid sample which is predominantly hydrophobic in nature. The method includes extracting water present in the hydrophobic fluid sample into an aprotic solvent (preferably consisting of acetonitrile ($CH_3CN$), dimethyl sulfoxide (($CH_3$)$_2$SO, also known as DMSO), or sulfolane ($C_4H_8O_2S$, also known as tetramethylene sulfone)) and deriving the moisture content of the resultant solvent from a measure of absorbance in the spectral band between 1615 $cm^{-1}$ and 1645 $cm^{-1}$ (most preferably in the band at or near 1633 $cm^{-1}$) for a spectrum derived from IR spectroscopy of the resultant solvent. This particular spectral band is due to the HOH bending vibration, which is specific to water only. The system includes an infrared spectrometer, a cell for holding and evaluating a sample, and a computer or workstation equipped with data analysis software for analyzing the data measured by the infrared spectrometer. The system can also include equipment for facilitating manual and/or automated operation of the infrared spectrometer, sample testing, and data collection.

As part of a calibration process, the infrared spectrometer and the data analysis software executing at the workstation are used to perform IR spectroscopy on an extraction solvent blank (the aprotic solvent itself) and on a number of solvent-water mixtures of predetermined water concentrations (referred to as calibration samples). The spectrum of the extraction solvent blank is used in conjunction with the respective spectrum for the number of calibration samples to derive differential spectrums for the number of calibration samples. The differential spectrums for the number of calibration samples are processed to derive corresponding final spectrums for the number of water samples. Preferably, such processing involves taking the second derivative (most preferably the 5-5 (gap-segment) second derivative) of the respective differential spectrum to derive the corresponding final spectrum. Absorbance values of the final spectrums in the spectral band between $1615$ cm$^{-1}$ and $1645$ cm$^{-1}$ (most preferably in the band at or near $1633$ cm$^{-1}$) are used to solve for parameters of a calibration equation that relates such absorbance values to unit moisture concentration (micrograms/gram ($\mu g/g$)). Unit moisture concentration for each respective calibration sample is derived by dividing the weight (in g) of water in the respective calibration sample by the product of $10^{-6}$ and the weight of the solvent (in g) in the respective calibration sample.

In order to characterize the moisture content of a hydrophobic fluid of interest, an extract-sample is produced by mixing the extraction solvent with a sample of the hydrophobic fluid of interest. The mixture is typically separated into phases, where the density of the extraction solvent used determines whether it is the bottom or the top phase. In the case of acetonitrile, it typically is the upper phase as it generally has a lower density than the materials from which the water is extracted. The moisture from the hydrophobic fluid of the bottom phase is extracted into the top phase solvent. The extract-sample is taken from the top phase. The infrared spectrometer and the data analysis software executing at the workstation are used to perform IR spectroscopy on the extract-sample. The spectrum of the extraction solvent blank (measured during the calibration process) is used in conjunction with the spectrum of the extract-sample to derive a differential spectrum for the extract-sample. The differential spectrum for the extract-sample is processed to derive a final spectrum for the extract-sample in a manner that mirrors the differential spectrum processing of the calibration process. Preferably, such processing involves taking the second derivative (most preferably the 5-5 (gap-segment) second derivative) of the differential spectrum to derive the final spectrum of the extract-sample. The absorbance value of the final spectrum in the spectral band between $1615$ cm$^{-1}$ and $1645$ cm$^{-1}$ (most preferably in the mid infra-red band at or near $1633$ cm$^{-1}$) is input to the calibration equation derived by the calibration process, which outputs a unit moisture concentration ($\mu g/g$) that reflects the moisture content of the extract-sample. Such moisture was extracted from the hydrophobic fluid into the extract-sample. This unit moisture concentration ($\mu g/g$) is multiplied by the ratio of the weight (in g) of the solvent in the extract-sample to the weight (in g) of hydrophobic fluid mixed with the solvent in preparing the extract-sample in order to derive a measure of moisture concentration (ppm) in the hydrophobic fluid of interest.

The miscibility of the hydrophobic fluid of interest in the extraction solvent can contribute to absorbance in the bands where the water measurements are made (i.e., in the spectral band between $1615$ cm$^{-1}$ and $1645$ cm$^{-1}$). In accordance with the present invention, the methodology of the present invention can compensate for this effect by preparing a mixture of the hydrophobic fluid of interest and deuterium oxide ($D_2O$), which is referred to as a sample blank. The $D_2O$ removes $H_2O$ (HOH) bending absorptions from the spectrum of the hydrophobic fluid of interest in the mid infra-red band between $1615$ cm$^{-1}$ and $1645$ cm$^{-1}$ (most preferably in the mid infra-red band at or near $1633$ cm$^{-1}$). Thus, the differential spectrum obtained by subtracting the spectrum of the sample blank from the spectrum of the extract-sample will provide absorption proportional to the moisture content of the extract-sample. More specifically, FTIR spectroscopic testing is performed on the sample blank in order to generate a spectrum for the sample blank. The spectrum of the extract-sample (measured during the sample analysis process) is used in conjunction with the spectrum of the sample blank to derive a differential spectrum for the extract-sample. The differential spectrum for the extract-sample is processed to derive a final spectrum for the extract-sample in a manner that mirrors the differential spectrum processing of the calibration process. Preferably, such processing involves taking the second derivative (most preferably the 5-5 (gap-segment) second derivative) of the differential spectrum to derive the final spectrum of the extract-sample. The absorbance value of the final spectrum in the mid infra-red band between $1615$ cm$^{-1}$ and $1645$ cm$^{-1}$ (most preferably in the mid infra-red band at or near $1633$ cm$^{-1}$) is input to the calibration equation derived by the calibration process, which outputs a unit moisture concentration ($\mu g/g$) for the extract-sample that reflects the contributions of both the water extracted from the hydrophobic fluid of interest and the water initially present in the extraction solvent, whereas all non-water spectral contributions of the hydrophobic fluid of interest are eliminated by these operations. This unit moisture concentration ($\mu g/g$) can be corrected for the background unit moisture concentration ($\mu g/g$), which reflects the contribution of the water initially present in the extraction solvent. For example, the background unit moisture concentration can be derived through the use of a $D_2O$ blank as described herein and then subtracted from the unit moisture concentration of the extract-sample. The resulting unit moisture concentration value ($\mu g/g$) is multiplied by the ratio of the weight (in g) of the solvent in the extract-sample to the weight (in g) of hydrophobic fluid mixed with the solvent in preparing the extract-sample in order to derive a measure of moisture concentration (ppm) in the hydrophobic fluid of interest. These operations compensate for miscibility of the hydrophobic fluid in the extraction solvent and for background water content in the solvent.

Acetonitrile, dimethyl sulfoxide, and sulfolane are particularly suitable as an extraction solvent for moisture because each compound is (1) aprotic and does not interfere with $D_2O$ analysis, (2) polar, and (3) largely immiscible with most hydrophobic samples and does not absorb strongly in the regions of the mid-IR spectrum where water absorbs, thus allowing for low levels of moisture to be detected.

The accuracy and sensitivity of the above method is dependent upon the relative dryness (lack of water content) of the extract solvent. For example, for hydrophobic fluids having water content greater than 100 ppm, the extraction solvent having moisture content less than 200 ppm is generally sufficient. However, for hydrophobic fluids (such as transformer oils) having water less than 100 ppm, the extraction solvent having moisture content less than 60 ppm is generally sufficient. If need be, the extraction solvent may be dried to remove water content by a variety of methods, including distillation, use of molecular sieves or calcium hydride, or other procedures commonly used for drying solvents.

In the preferred embodiment, the moisture content (e.g., the "dryness") of the extraction solvent is determined by measuring spectral differences after the addition of deuterium oxide ($D_2O$) thereto, which removes $H_2O$ (HOH) bending absorptions from the spectrum of the extraction solvent in the mid infra-red band between 1615 $cm^{-1}$ and 1645 $cm^{-1}$ (most preferably in the mid infra-red band at or near 1633 $cm^{-1}$). Thus, the differential spectrum obtained by subtracting the spectrum of the $D_2O$ treated extraction solvent from the spectrum of the extraction solvent blank will provide absorption proportional to the moisture content of the solvent. This measure can be used as a quality control procedure to ensure that the extract solvent is adequately dry. More specifically, a mixture of the extraction solvent and $D_2O$ is prepared. This solvent-$D_2O$ mixture is referred to herein as a $D_2O$ blank. FTIR spectroscopic testing is performed on the $D_2O$ blank in order to generate a spectrum for the $D_2O$ blank. The spectrum of the extraction solvent is used in conjunction with the spectrum of the $D_2O$ blank to derive a differential spectrum for the extraction solvent. The differential spectrum for the extraction solvent is processed to derive a final spectrum for the extraction solvent in a manner that mirrors the differential spectrum processing of the calibration process. Preferably, such processing involves taking the second derivative (most preferably the 5-5 (gap-segment) second derivative) of the differential spectrum to derive the final spectrum of the $D_2O$ blank. The absorbance value of the final spectrum in the mid infra-red band between 1615 $cm^{-1}$ and 1645 $cm^{-1}$ (most preferably in the mid infra-red band at or near 1633 $cm^{-1}$) is input to the calibration equation derived by the calibration process, which outputs a unit moisture concentration (μg/g) that is numerically equal to the moisture content (ppm) of the extraction solvent itself. This moisture concentration (ppm) of the extraction solvent itself can be evaluated to ensure that the extraction solvent is adequately dry. For characterizing hydrophobic fluids having water content greater than 100 ppm, the extract solvent having moisture content less than 200 ppm is generally sufficient. However, for characterizing hydrophobic fluids (such as transformer oils) having water less than 100 ppm, the extraction solvent having moisture content less than 60 ppm is generally sufficient. The unit moisture concentration of the extraction solvent itself can also be used to derive a background unit moisture concentration that compensates for the background water content of the extraction solvent as described herein.

In the preferred embodiment of the invention, $D_2O$ is added to an extract-sample to prepare a sample blank, and/or $D_2O$ is added to the extraction solvent to prepare a $D_2O$ blank. Dilution from this addition of $D_2O$ or dilution of the extraction solvent by the hydrophobic fluid dissolved in it can be compensated for by calculating a dilution correction factor (DCF) for the spectrums of the calibration samples, the extract-sample, the sample blank, and the $D_2O$ blank (if used). More particularly, the DCF is calculated by dividing the height of a particular solvent band (preferably at or near 2070 $cm^{-1}$ for acetonitrile) relative to a baseline (preferably through a number of anchor points at or near 2080 $cm^{-1}$ and 2040 $cm^{-1}$, respectively) for the spectrum of the extraction solvent blank by the height of the particular solvent band relative to the baseline for the respective spectrum (one of the calibration samples, the extract-sample, the sample blank, or the $D_2O$ blank). The respective spectrum is multiplied by the corresponding DCF to provide a corrected spectrum. The spectrum of the extraction solvent blank is subtracted from the corrected spectrums to derive differential spectrums for the calibration samples and the extract-sample as required. The corrected spectrum of the $D_2O$ blank is subtracted from the spectrum of the extraction solvent blank to derive a differential spectrum for the extraction solvent as required. The corrected spectrum of the sample blank is subtracted from the corrected spectrum of the extract-sample to derive a differential spectrum for the extract-sample as required.

Advantageously, the present method characterizes the moisture content of a generally hydrophobic sample. As further discussed below, by extracting moisture present in the sample with certain aprotic solvents, spectral interferences from the sample during FTIR analysis are minimized. Moreover, the moisture extraction approach of the present invention can provide substantial gains in sample analytical throughput for a given system.

The method of the invention also provides significant flexibility to modify the analytical range and sensitivity of the calibration and/or analyses by simple adjustment of the calibration, sample weights, extraction solvent volumes, splitting of the sample, or combinations thereof.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
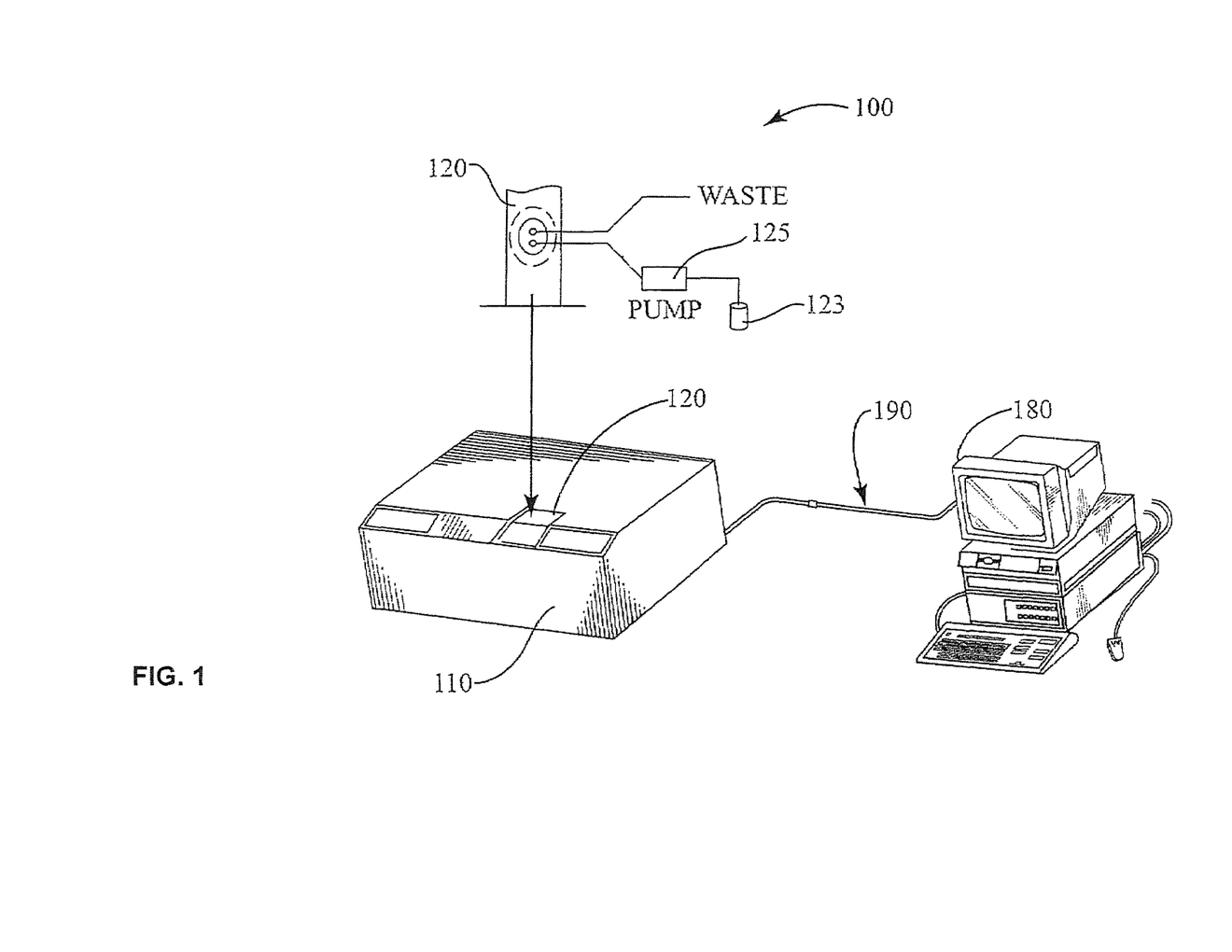
FIG. 1 is a schematic view of a system for performing FTIR spectroscopy that can embody the present invention.

Turning to FIG. 1, a system 100 for performing spectroscopic analysis of a sample includes a spectrometer 110 for collecting IR absorption data. A WorkIR series IR spectrometer 110 (which is preferably equipped with a deuterated triglycine sulfate (DTGS) detector) as sold commercially by ABB Analytical of Quebec, Canada can be used. Other commercially-available IR spectrometers can also be used. A flow-through sample cell 120 is provided into which fluids from a sample vial may be loaded manually, such as by vacuum aspiration into the cell 120. Alternatively, the fluid sample may be loaded into the sample cell 120 in an automated manner, for example with a minipump 125 used in conjunction with an autosampler 123 as shown. In the preferred embodiment, the sample cell 120 is realized by a 1000-μm CaF$_2$ transmission flow cell. Data acquired by the spectrometer 110 is communicated to a computer or workstation 180 via a data interface 190 (e.g., USB data interface or the like) for processing and analysis in accordance with the present invention. The computer 180 preferably includes a complete and fully integrated software package which is run at the computer 180 for analyzing the data and outputting information to a user (e.g., via a printer and/or on-screen). The software should at a minimum be able to perform acquisition of IR spectral data measured by the spectrometer 110 as well as Fourier transform analysis and quantification of such IR spectral data.

In the preferred embodiment, the spectral acquisition parameters for the apparatus 100 are set to the following:
resolution—4 cm$^{-1}$;
apodization—triangular;
gain—1;
spectral acquisition time—approximately 32 seconds; and
number of co-added scans—32 or 16, depending on whether the spectrometer 110 collects single-sided or double-sided interferograms).

Figure 2A:
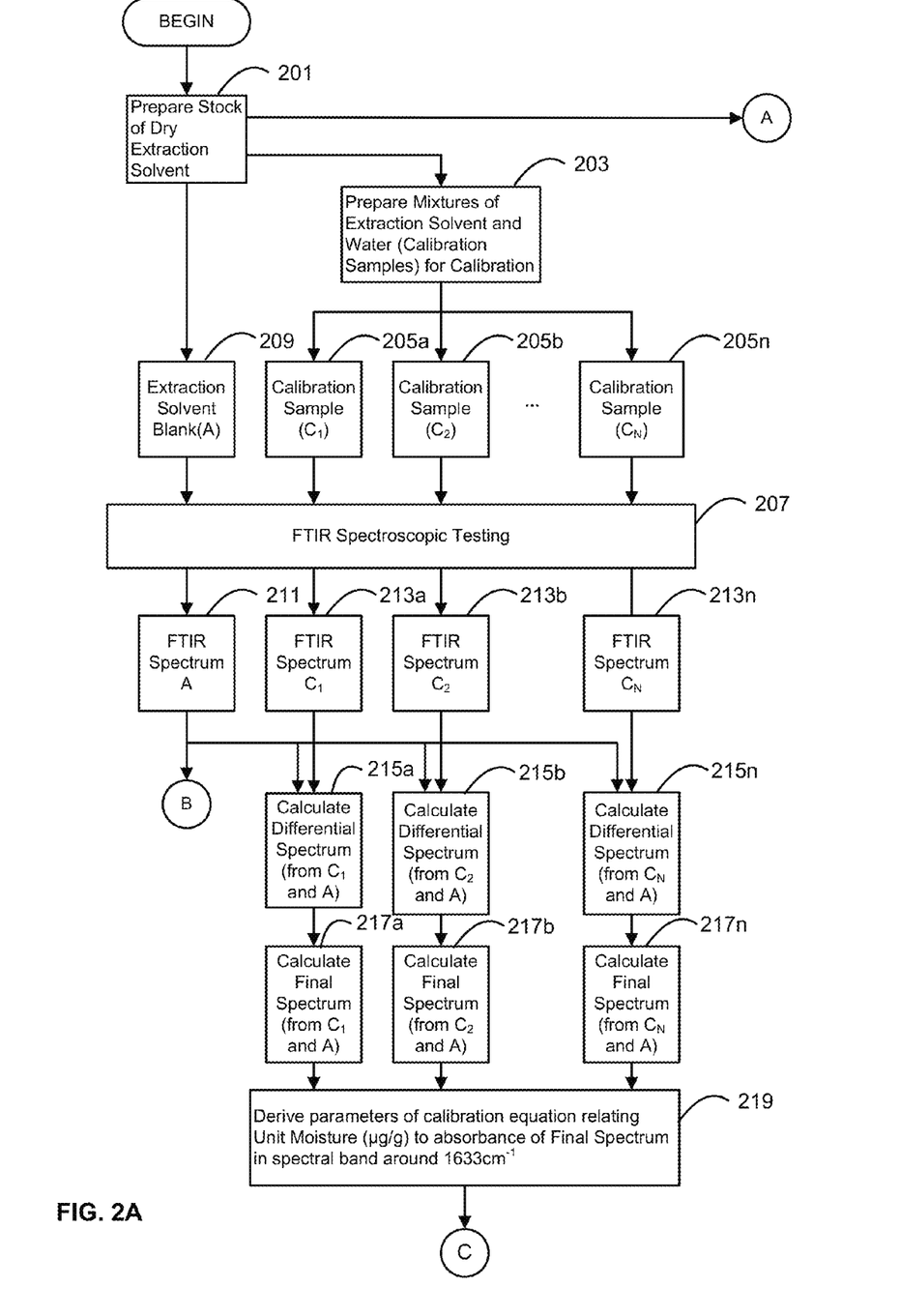
FIGS. 2A and 2B, collectively, is a flowchart showing the workflow for characterizing moisture content of a fluid sample in accordance with the present invention.
Figure 2B:
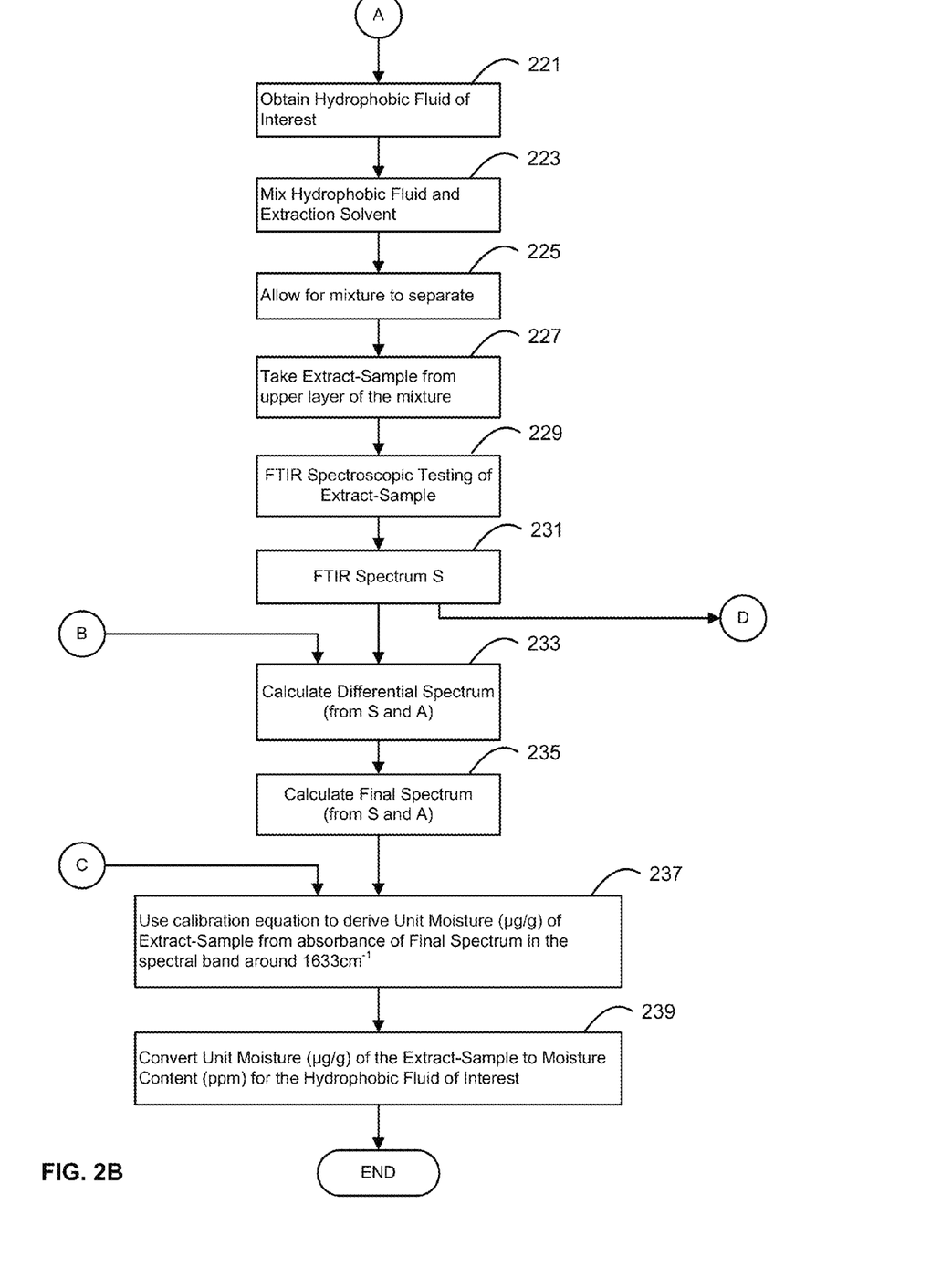

The system 100 of FIG. 1 is used to perform the methodology 200 of FIGS. 2A and 2B for generating data characterizing the moisture content of a generally hydrophobic fluid sample in accordance with the present invention. The method begins at block 201 with the preparation of an acetonitrile solvent. The moisture content of the acetonitrile solvent is preferably limited in nature (preferably less than 200 parts per million or less) in order to ensure accuracy of the analysis. Moreover, suitable material handling operations of the acetonitrile solvent should be taken to preventingress of atmospheric moisture during dispensing, sample extraction, and analysis. In the preferred embodiment, the acetonitrile solvent is prepared by adding acetonitrile (CH$_3$CN) containing less than 100 ppm of water) from Sigma-Aldrich of Oakville, ON, Canada to a two liter bottle containing dry molecular sieves (which have been heated to 230° C. for a minimum of two hours and cooled in a desiccator). A re-pipette dispenser is set up over the bottle. Care should be taken to ensure that the re-pipette dispenser is well seated so as to be airtight. The air intake of the re-pipette dispenser is connected via Tygon tubing to a 250-mL gas washing fitted cylinder bottle containing dry molecular sieves through which intake air will be pre-dried. The inlet air Tygon tubing is clamped shut except when dispensing. The acetonitrile solvent can be dried with dry molecular sieves or other suitable means to reduce the water content of the acetonitrile prior to introduction into the dispenser-capped bottle.

In alternate embodiments, dimethyl sulfoxide ((CH$_3$)$_2$SO) or sulfolane (C$_4$H$_8$O$_2$S) or other suitable aprotic solvent can be used as a substitute for the dry acetonitrile solvent.

Acetonitrile, dimethyl sulfoxide, and sulfolane are particularly suited for use in the present invention because each compound is (1) aprotic and does not interfere with D$_2$O analysis, (2) polar, and (3) largely immiscible with most hydrophobic samples and does not absorb strongly in the regions of the mid-IR spectrum where water absorbs, thus allowing for low levels of moisture to be detected.

At block 203, the aprotic solvent of block 201 is mixed with distilled water at different water concentration levels to produce a number of solvent-water mixtures (referred to herein as "calibration samples" or "C$_1$, C$_2$, . . . C$_N$" and labeled 205A, 205B . . . 205N in FIG. 2A) for calibration purposes. The calibration samples 205A, 205B . . . 205N are preferably stored in a suitable crimp-cap glass vial. In the preferred embodiment, the calibration samples 205A, 205B . . . 205N are prepared from a stock solution of approximately 100 grams of the solvent of block 201 and approximately 0.1 g of distilled water. The stock solution is intended to be approximately 100 milliliters and contain approximately 1000 ppm of water. The exact concentration of water in the stock solution can be calculated from the ratio of the weight of the added distilled water to the weight of the added solvent of block 201. Specifically, the exact concentration (in ppm) of water in the stock solution can be calculated by multiplying the weight ratio of distilled water to solvent (g/g) by 10$^6$. The stock solution is then diluted with the solvent of block 201 at different weight concentrations to provide the desired calibration samples. An example of the dilutions for six calibration samples of acetonitrile solvent is shown in Table A below.

TABLE A

| Mixture | Target Moisture (ppm) | Stock (g) | Dry acetonitrile (g) | Total (g) |
|---|---|---|---|---|
| C1 | 1000 | 20 | 0 | 20 |
| C2 | 500 | 10 | 10 | 20 |
| C3 | 250 | 5 | 15 | 20 |
| C4 | 125 | 2.5 | 17.5 | 20 |
| C5 | 60 | 1.25 | 18.75 | 20 |
| C6 | 30 | 0.625 | 19.375 | 20 |

Other suitable target moisture levels can be used as desired. For each calibration sample, the water concentration of the calibration sample is calculated from the water concentration of the stock solution and the weight of the solvent in the mixture per equation [1] below.

$$\text{concentration of water (ppm) in calibration sample} = \\ (\text{g of stock})*(\text{concentration of water (ppm) in stock}) / (\text{g stock} + \text{g dry solvent}). \quad [1]$$

In block 207, the system 100 is used to perform FTIR spectroscopic analysis on a sample of the solvent of block 201 (referred to herein as an "extraction solvent blank" or "(A)" and labeled 209 in FIG. 2A as well as on each one of the calibration samples 205A, 205B . . . 205N. The FTIR spectroscopic analysis of the extraction solvent blank A produces an FTIR spectrum A (labeled 211) at the computer 180. The FTIR spectroscopic testing of the calibration sample C$_1$ produces an FTIR spectrum C$_1$ (labeled 213A) at the computer 180. The FTIR spectroscopic testing of the calibration sample C$^2$ produces an FTIR spectrum C$^2$ (labeled 213B) at the computer 180. FTIR spectrums (213C to 213N) are generated for all of the remaining calibration samples C$_3$ . . . C$_N$ by the computer 180. In the preferred embodiment, a set-up procedure is performed as part of the analysis of each sample. The set-up procedure typically involves cleaning the sample cell of the spectrometer 110 (for example, by washing with a solvent and drying by flushing the cell with air), performing a background scan on the spectrometer 110, loading the fluid sample into the sample cell of the spectrometer 110, and configuring the operating parameters for the spectrometer 110 and computer 180. After the set-up procedure is complete, the spectrometer 110 and computer 180 are operated to perform the experiment, collect the IR absorption data resulting from the experiment, and perform Fourier Transform processing on the collected IR absorption data to generate the FTIR spectrum for the respective sample.

In block 215A, the computer 180 calculates a differential spectrum for the calibration sample C$_1$ from the FTIR spectrum C$_1$ (labeled 213A) and the FTIR spectrum A (labeled 211). In block 215B, the computer 180 calculates a differential spectrum for the calibration sample C$_2$ from the FTIR spectrum $C_2$ (labeled 213B) and the FTIR spectrum A (labeled 211). Similar operations are performed by the computer 180 in blocks 215C . . . 215N to calculate differential spectrums for the calibration samples $C_3$ . . . $C_N$. Details of preferred spectral processing in deriving the differential spectrums of block 215A . . . 215N are described below with respect to FIG. 5. Alternatively, other suitable spectral processing can be used.

In block 217A, the computer 180 processes the differential spectrum of block 215A to calculate a final spectrum for the calibration sample $C_1$. In block 217B, the computer 180 processes the differential spectrum of block 215B to calculate a final spectrum for the calibration sample $C_2$. Similar operations are performed by the computer 180 in blocks 217C . . . 217N to calculate final spectrums for the calibration samples $C_3$ . . . $C_N$. In the preferred embodiment, the final spectrum for the respective calibration sample is derived from a 5-5 (gap segment) second derivative of the corresponding differential spectrum. The gap-segment $2^{nd}$ derivative serves the purpose of providing a stable baseline to measure to, sharpens bands and helps separate any overlapping bands, which minimizes spectral interferences arising from the portion of the sample that is miscible with the extraction solvent used.

The 5-5 (gap-segment) second derivative of the differential spectrum for each respective calibration mixture is preferably computed as follows. First, the absorbance value A(i) at each data point i of the differential spectrum is replaced by the mean absorbance value for a segment of 5 data points centered at data point i by:

$$A(i)=[A(i-2)+A(i-1)+A(i)+A(i+1)+A(i+2)]/5 \quad [2]$$

A gap second derivative is then applied at each data point i by:

$$d^2A(i)/dx_2=[-2A(i)+A(i+2g)+A(i-2g)]/4g\Delta x \quad [3]$$

where $\Delta x$ is the data point spacing in units of wavenumbers, and g is set to 5 for the 5-5 (gap-segment) second derivative. The result at each data point i is multiplied by 100 to produce the final spectrum. It is noted that measurements made on this second-derivative spectrum are referred to as absorbance (Abs) measurements for the sake of simplicity.

For example, the final spectrum for the calibration sample $C_1$ is derived from a 5-5 (gap segment) second derivative of the differential spectrum of block 215A. Alternatively, other suitable spectral processing can be used. It may be noted that the spectral values output by blocks 217A . . . 217N may not be in absorbance units but are referred to as absorption measurements herein. It may also be noted that these measurements are not referenced to a spectral baseline point, because baseline offsets and tilts are not significant in second derivative spectra.

In block 219, the computer 180 utilizes the absorbance measurement of the final spectrums 217A, 217B . . . 217N for the mid infra-red band between 1615 $cm^{-1}$ and 1645 $cm^{-1}$ (preferably at or near 1633 $cm^{-1}$) to derive parameters of a calibration equation relating unit moisture to absorbance of the final spectrum in this particular mid infra-red band. Unit moisture is a weight fraction (preferably in µg/g) of moisture to the solvent. In the preferred embodiment, the computer 180 derives unit moisture values (µg/g) for the calibration samples $C_1$ . . . $C_N$ from the weight of distilled water and the weight of solvent in the corresponding calibration samples by Eq. [4] as follows:

$$\text{Unit Moisture (in µg/g)}=10^6 \times M/WA \quad [4]$$

where M is the weight (in g) of distilled water in the respective calibration sample, and WA is the weight of solvent (in g) in the respective calibration sample.

The computer 180 can carry out linear regression on the unit moistures for the calibration samples and the absorbance of the final spectrums 215A, 215B . . . 215N for the particular mid infra-red band and to obtain the parameters (a, b) of a best fit equation of the form:

$$\text{Unit Moisture (µg/g)}=a+b^*\text{Abs}_{(1633cm^{-1})}. \quad [5]$$

Importantly, the calibration equation relating unit moisture to absorbance for the particular mid infra-red band is universal in that it is independent of the sample weight or extraction solvent volume used in the analysis of samples.

In block 221, a sample of a generally hydrophobic fluid of interest is obtained. The hydrophobic fluid sample can be a lubricant, an edible oil, or a fuel such as biodiesel.

In block 223, the hydrophobic fluid of block 221 is mixed with the solvent of block 201 at or near a predetermined concentration. In the preferred embodiment, approximately 30 grams of the hydrophobic fluid of block 221 is mixed with approximately 15 mL of the extraction solvent of block 201. The mixture is preferably stored in a suitable 50-mL vial with a Mylar-lined septum cap. The weight (in grams ±0.0001 g) of the hydrophobic fluid of the mixture is measured and recorded by the computer 180. Similarly the weight in grams of the solvent of the mixture is measured and recorded by the computer 180. The mixture is preferably agitated (for example, by a shaker) for a predetermined period of time (e.g., 30 minutes).

In block 225, the mixture is allowed to stand for a period of time (e.g., 10 minutes) or centrifuged to permit the mixture to separate with the oil-immiscible solvent on top of the hydrophobic fluid. Moreover, as a result of the mixing and separation process, moisture (water) is extracted from the hydrophobic fluid and captured in the solvent phase (the supernatant of the separated mixture).

In block 227, an extract-sample is taken from the upper 12 mL (the solvent phase) of the separated mixture of block 225.

In block 229, the system 100 is used to perform FTIR spectroscopic analysis on the extract-sample to produce an FTIR spectrum S (labeled 231). In the preferred embodiment, a set-up procedure is performed as part of the analysis of the extract-sample. The set-up procedure typically involves cleaning the sample cell of the spectrometer 110 (for example, by washing with a solvent and drying by flushing the cell with air), performing a background scan on the spectrometer 110, loading the extract-sample into the sample cell of the spectrometer 110, and configuring the operating parameters for the spectrometer 110 and computer 180. After the set-up procedure is complete, the spectrometer 110 and computer 180 are operated to perform the experiment, collect the IR absorption data resulting from the experiment, and perform Fourier Transform processing on the collected IR absorption data to generate the FTIR spectrum for the extract-sample.

In block 233, the computer 180 calculates a differential spectrum for the extract-sample from the FTIR spectrum S (labeled 231) and the FTIR spectrum A (labeled 211). Details of preferred spectral processing in deriving the differential spectrum of block 231 are described below with respect to FIG. 5. This preferred spectral processing compensates for any dilution of the extraction solvent by the hydrophobic fluid dissolved in it. Alternatively, other suitable spectral processing can be used.

In block 235, the computer 180 processes the differential spectrum of block 233 to calculate a final spectrum for the extract-sample. In the preferred embodiment, the final spectrum for the extract-sample is derived from a 5-5 (gap segment) second derivative of the differential spectrum of block 233. The gap-segment $2^{nd}$ derivative serves the purpose of providing a stable baseline to measure to, sharpens bands and helps separate any overlapping bands, which minimizes spectral interferences arising from any portion of the sample that is miscible with the extraction solvent used. Alternatively, other suitable spectral processing can be used. It may be noted that the spectral values output by block 235 may not be in absorbance units but are referred to as absorption measurements herein. It may also be noted that these measurements are not referenced to a spectral baseline point, because baseline offsets and tilts are not significant in second derivative spectra.

In block 237, the computer 180 utilizes the absorbance measurements of the final spectrum of block 235 for the mid infra-red band between 1615 cm$^{-1}$ and 1645 cm$^{-1}$ (preferably at or near 1633 cm$^{-1}$) as an input to the calibration equation of block 219 to calculate unit moisture (μg/g) of the extract-sample. Importantly, the calibration equation relating unit moisture (μg/g) to absorbance for the particular mid infra-red band is universal in that it is independent of the sample weight or extraction solvent volume used in the analysis of samples.

In block 239, computer 180 converts the unit moisture (μg/g) of the extract-sample of block 235 to moisture content (in ppm) in the hydrophobic fluid of interest. In the preferred embodiment, the conversion of block 239 involves multiplying the unit moisture (μg/g) of the extract-sample as derived in block 237 by the ratio of the weight (in grams) of solvent mixed with the hydrophobic fluid in block 223 to the weight (in grams) of hydrophobic fluid mixed with the solvent in block 223. The weight of the solvent mixed with the hydrophobic fluid in block 223 can be measured or derived from a measurement of the volume of the solvent mixed with the hydrophobic fluid in block 223 and the density of solvent (e.g., 0.777 g/mL for acetonitrile). The moisture content (in ppm) of the sample can be stored by the computer 180 and output to the user as desired. The moisture content of the sample as stored and output by the computer 180 can also be converted to other suitable units of concentration, such as weight percentage, mole fraction, molarity, and molality.

Blocks 221-239 can be performed by automated (or semi-automated) fluid handling and measuring equipment as is well known in the art. Parts of blocks 221-239 can be performed by manual fluid handling and measuring operations as is well known in the art.

In the preferred embodiment of the present invention, the dryness of the solvent of block 201 can be analyzed by FTIR analysis to ensure it is within the limits required by the analysis. Preferably, such analysis is carried out prior to preparing the calibration mixtures (block 203) and the sample mixture (block 223). It can also be carried out periodically (for example, once a day) to ensure the dryness of the solvent remains within the limits required by the analysis.

Figure 3:
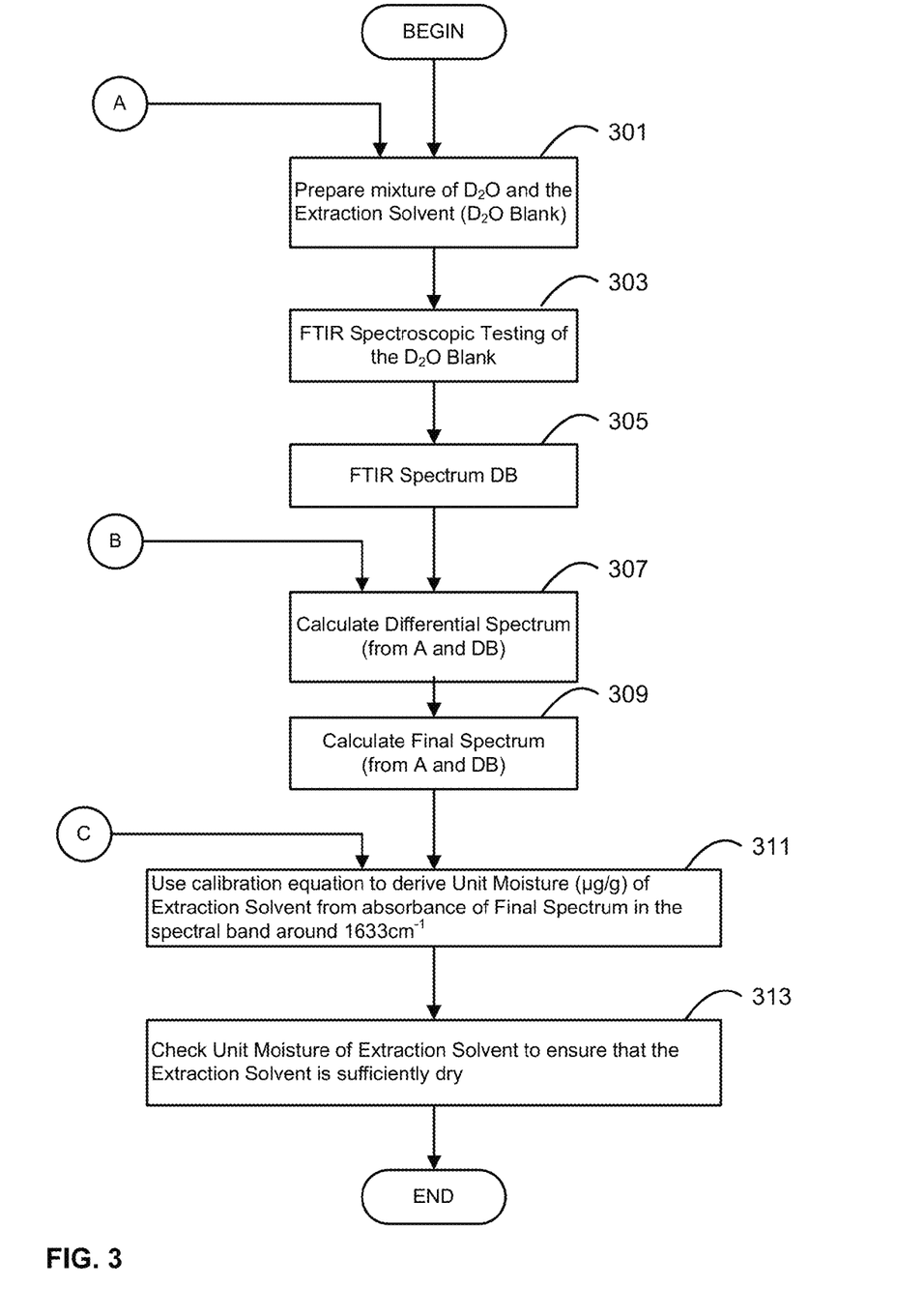
FIG. 3 is a flowchart showing the workflow for analyzing a $D_2O$ blank for use in conjunction with the workflow of FIGS. 2A and 2B.

An illustrative embodiment of FTIR analysis for measuring and evaluating the dryness of the solvent of block 201 is set forth in FIG. 3, which begins in block 301 by preparing a mixture of deuterium oxide ($D_2O$) and the extraction solvent of block 201 at or near a predetermined concentration. This $D_2O$-solvent mixture is referred to as a $D_2O$ blank. In the preferred embodiment, the $D_2O$ blank is realized by mixing approximately 300 μL of deuterium oxide with approximately 15 mL of the solvent of block 201. The mixture is preferably stored in a suitable vial with a Mylar-lined septum cap.

In block 303, the system 100 is used to perform FTIR spectroscopic analysis on the $D_2O$ blank to produce an FTIR spectrum DB (labeled 305). In the preferred embodiment, a set-up procedure is performed as part of the analysis of the $D_2O$ blank. The set-up procedure typically involves cleaning the sample cell of the spectrometer 110 (for example, by washing with a solvent and drying by flushing the cell with air), performing a background scan on the spectrometer 110, loading the $D_2O$ blank into the sample cell of the spectrometer 110, and configuring the operating parameters for the spectrometer 110 and computer 180. After the set-up procedure is complete, the spectrometer 110 and computer 180 are operated to perform the experiment, collect the IR absorption data resulting from the experiment, and perform Fourier Transform processing on the collected IR absorption data to generate the FTIR spectrum DB for the $D_2O$ blank.

In block 307, the computer 180 calculates a differential spectrum for the $D_2O$ blank from the FTIR spectrum DB (labeled 305) and the FTIR spectrum A (labeled 211). Details of preferred spectral processing in deriving the differential spectrum of block 307 are described below with respect to FIG. 5. Alternatively, other suitable spectral processing can be used.

In block 309, the computer 180 processes the differential spectrum of block 307 to calculate a final differential spectrum for the extraction solvent. In the preferred embodiment, the final differential spectrum for the extraction solvent is derived from a 5-5 (gap segment) second derivative of the differential spectrum of block 307. The gap-segment $2^{nd}$ derivative serves the purpose of providing a stable baseline to measure to, sharpens bands and helps separate any overlapping bands, which minimizes spectral interferences arising from the portion of the sample that is miscible with the extraction solvent used. Alternatively, other suitable spectral processing can be used. It may be noted that the spectral values output by block 309 may not be in absorbance units but are referred to as absorption measurements herein. It may also be noted that these measurements are not referenced to a spectral baseline point, because baseline offsets and tilts are not significant in second derivative spectra.

In block 311, the computer 180 utilizes the absorbance of the final spectrum of block 309 for the mid infra-red band between 1615 cm$^{-1}$ and 1645 cm$^{-1}$ (preferably at or near 1633 cm$^{-1}$) as an input to the calibration equation of block 219 to calculate unit moisture (μg/g) of the extraction solvent of block 201.

Figure 4:
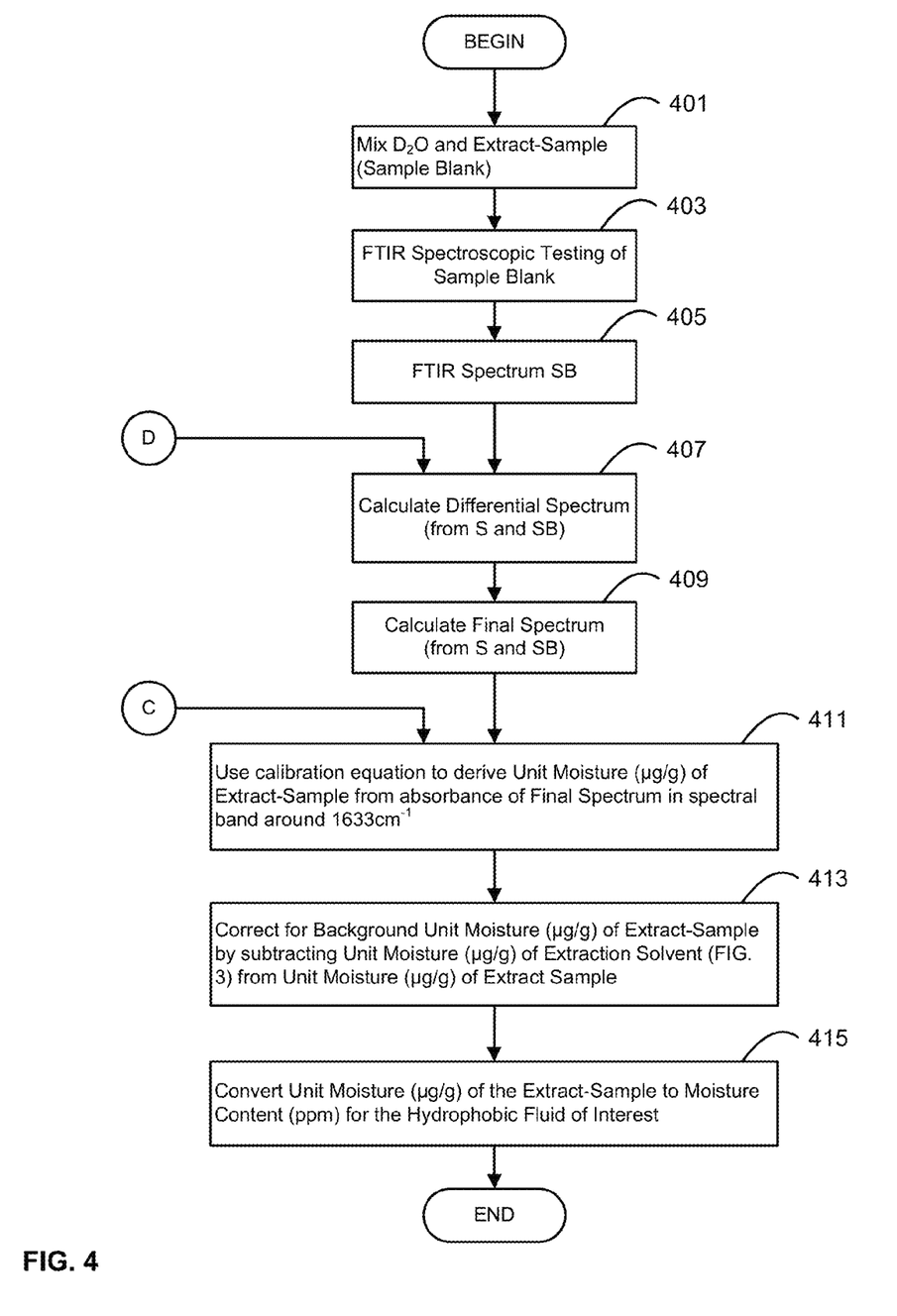
FIG. 4 is a flowchart showing the workflow for analyzing a sample blank for use in conjunction with the workflow of FIGS. 2A and 2B.

In block 313, the unit moisture (μg/g) of the extraction solvent of block 201 (as measured in block 311), which is numerically equal to the moisture concentration (in ppm) of the extraction solvent, is reported to the user for evaluation. If this moisture concentration (in ppm) exceeds the desired low limit for the analysis (for example, exceeds 200 ppm), the user can dry the solvent of block 201 (for example with dry molecular sieves) and repeat the analysis of blocks 301-313 to ensure the dryness of the solvent is within limits required by the analysis. The unit moisture (in μg/g) of the extraction solvent of block 201 (as measured in block 311) can also be used to derive a background unit moisture concentration that compensates for the background water content of the extraction solvent as described herein (FIG. 4).

The workflow of FIGS. 2A and 2B can be adapted to compensate for miscibility (matrix effects) of the hydrophobic fluid with the extraction solvent, which is suitable for analyzing fluid samples that are significantly miscible in the extraction solvent. In the preferred embodiment, the compensation of such matrix effects employs FTIR analysis of the extract-sample to which deuterium oxide ($D_2O$) has been added in the amount of 20 μl/ml of extract-sample for each 1000 ppm of moisture expected to be present in the extract-sample. An illustrative embodiment of such analysis is set forth in FIG. 4, which begins in block 401, the extract-sample is split into two portions (or duplicate extract-samples are prepared). Deuterium oxide ($D_2O$) is added to one half of the extract-sample by mixing 7.5 ml of the original 15 ml of extract-sample with 150 μl of deuterium oxide (or, if duplicates are prepared, 300 μl is added to 15 ml of extract-sample). The $D_2O$-treated portion of the extract-sample is termed the $D_2O$ sample blank or sample blank. Block 401 can be performed manually. Alternatively, block 401 (or parts of these operations) can be performed by automated (or semi-automated) fluid handling and measuring equipment as is well known in the art.

In block 403, the system 100 is used to perform FTIR spectroscopic analysis on the sample blank to produce an FTIR spectrum SB (labeled 405). In the preferred embodiment, a set-up procedure is performed as part of the analysis of the sample blank. The set-up procedure typically involves cleaning the sample cell of the spectrometer 110 (for example, by washing with a solvent and drying by flushing the cell with air), performing a background scan on the spectrometer 110, loading the sample blank into the sample cell of the spectrometer 110, and configuring the operating parameters for the spectrometer 110 and computer 180. After the set-up procedure is complete, the spectrometer 110 and computer 180 are operated to perform the experiment, collect the IR absorbance data resulting from the experiment, and perform Fourier Transform processing on the collected IR absorbance data to generate the FTIR spectrum SB for the sample blank.

In block 407, the computer 180 calculates a differential spectrum for the sample blank from the FTIR spectrum SB (labeled 405) and the FTIR spectrum S (labeled 231). Details of preferred spectral processing in deriving the differential spectrum of block 407 are described below with respect to FIG. 5.

By treating the fluid sample with deuterium oxide ($D_2O$), $H_2O$ (HOH) bending absorptions are removed from the spectrum of the extract-sample by the exchange reaction similar to the reaction between $D_2O$ and the extraction solvent as described below. The removal of these $H_2O$ (HOH) bending absorptions influences the absorbance spectrum of the Sample Blank in the mid infra-red band between 1615 $cm^{-1}$ and 1645 $cm^{-1}$ (most preferably in the mid infra-red band at or near 1630 $cm^{-1}$). Thus, the differential spectrum obtained by subtracting the spectrum of the sample blank from the spectrum of the extract-sample will provide absorbance proportional to the moisture content of the extract-sample, reflecting the contributions of both the water extracted from the hydrophobic fluid of interest and the water initially present in the extraction solvent, whereas all non-water spectral contributions of the hydrophobic fluid of interest are eliminated by these operations.

In block 409, the computer 180 processes the differential spectrum of the sample blank of block 407 to calculate a final spectrum for the extract-sample. In the preferred embodiment, the final spectrum for the extract-sample is derived from a 5-5 (gap segment) second derivative of the differential spectrum of block 407. The gap-segment $2^{nd}$ derivative serves the purpose of providing a stable baseline to measure to, sharpens bands and helps separate any overlapping bands, which minimizes spectral interferences arising from the portion of the sample that is miscible with the extraction solvent used. Alternatively, other suitable spectral processing can be used.

In block 411, the computer 180 utilizes the absorbance of the final spectrum of block 409 for the mid infra-red band between 1615 $cm^{-1}$ and 1645 $cm^{-1}$ (preferably at or near 1633 $cm^{-1}$) as an input to the calibration equation of block 217 to calculate unit moisture (μg/g) of the extract-sample. Importantly, the calibration equation relating unit moisture to absorbance for the particular mid infra-red band is universal in that it is independent of the sample weight or extraction solvent volume used in the analysis of samples.

In block 413, the unit moisture (μg/g) of the $D_2O$ blank of block 311 is subtracted from the unit moisture (μg/g) of the extract-sample to correct for the contribution of the water content of the extraction solvent of block 201 to the absorbance in the particular mid infra-red band between 1615 $cm^{-1}$ and 1645 $cm^{-1}$ (preferably at or near 1633 $cm^{-1}$) for the final spectrum of block 409.

In block 415, the corrected unit moisture (μg/g) of the extract-sample is converted to the moisture concentration (in ppm) for the fluid sample. In the preferred embodiment, the conversion of block 415 involves multiplying the corrected unit moisture (μg/g) of the extract-sample as derived in block 413 by the ratio of the weight (in grams) of extraction solvent in the sample mixture (block 223) to the weight (in g) of the hydrophobic fluid in the sample mixture (block 223). The weight of the extraction solvent in the sample mixture can be measured or derived from a measurement of the volume of the extraction solvent in the sample mixture (block 223) and the density of the extraction solvent (e.g., 0.777 g/mL for acetonitrile).

The moisture content derived in block 415 can be stored by the computer 180 and output to the user as desired. The moisture content of the hydrophobic fluid of interest as stored and output by the computer 180 can also be converted to other suitable units of concentration, such as weight percentage, mole fraction, molarity, and molality.

Figure 5:
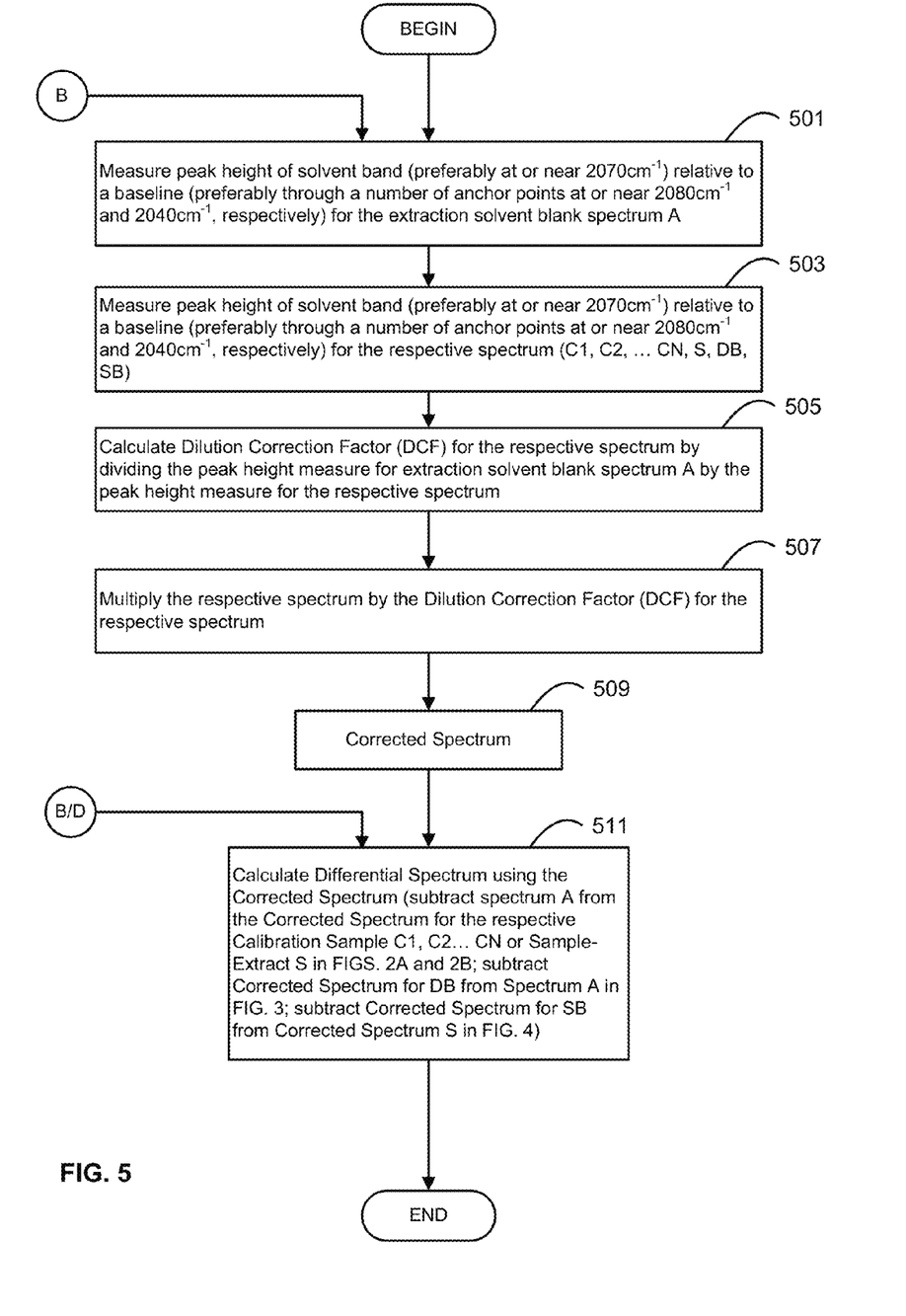
FIG. 5 is a flowchart showing operations for calculating a differential spectrum that can be used in conjunction with the workflow of FIGS. 2A, 2B, 3, and 4; the differential spectrum generated by the operations of FIG. 5 compensate for dilution of the extraction solvent by the hydrophobic fluid or $D_2O$ dissolved in it or for dilution of the sample blank by the $D_2O$ dissolved in it.

In an illustrative embodiment, the workflows of FIGS. 2A, 2B, 3 and 4 generate differential spectrums in a manner that compensates for dilution of the extraction solvent by the hydrophobic fluid dissolved in it or for dilution of the extraction solvent by $D_2O$ in the $D_2O$ blank or for dilution of the sample blank by the $D_2O$ dissolved in it. Details of preferred operations for generating such differential spectrums is shown in FIG. 5, which begins in block 501 where the computer 180 measures the peak height of a particular solvent band (preferably at or near 2070 $cm^{-1}$ for acetonitrile) relative to a baseline (preferably through a number of anchor points at or near 2080 $cm^{-1}$ and 2040 $cm^{-1}$, respectively) for the FTIR spectrum A of block 211.

In block 503, the computer 180 measures the peak height of the particular solvent band (preferably at or near 2070 $cm^{-1}$ for acetonitrile) relative to a baseline (preferably through a number of anchor points at or near 2080 $cm^{-1}$ and 2040 $cm^{-1}$, respectively) for a respective spectrum (C1, C2 ... CN, S, DB, or SB).

In block 505, the computer 180 calculates a dilution correction factor (DCF) for the respective spectrum (C1, C2 ... CN, S, DB or SB) by dividing the peak height of block 501 by the peak height of block 503.

In block 507, the computer 180 multiplies the respective spectrum (C1, C2 ... CN, S, DB or SB) by the DCF of block 505 to derive a respective corrected spectrum 509.

In block 511, the computer 180 calculates a differential spectrum using the corrected spectrum 509. This differential spectrum compensates for any dilution of the extraction solvent by the hydrophobic fluid dissolved in it or for dilution of the sample blank by the $D_2O$ dissolved in it. In the workflow of FIGS. 2A and 2B, the spectrum of the extraction solvent blank is subtracted from the corrected spectrums to derive differential spectrums for the calibration samples and the extract-sample as required. In the workflow of FIG. 3, the corrected spectrum of the $D_2O$ blank is subtracted from the spectrum of the extraction solvent blank to derive a differential spectrum for the extraction solvent as required. In the workflow of FIG. 4, the corrected spectrum of the sample blank is subtracted from the corrected spectrum of the extract-sample to derive a differential spectrum for the extract-sample as required.

Figure 6:
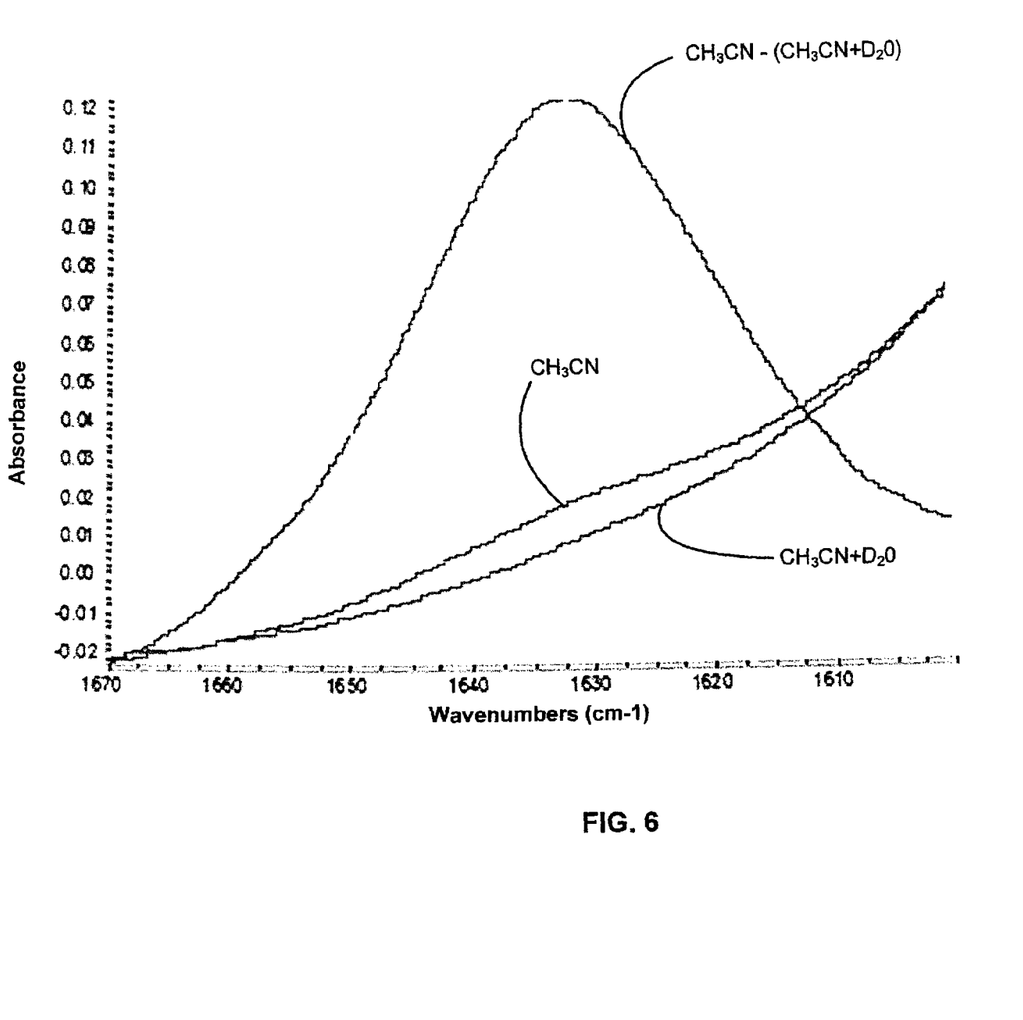
FIG. 6 is a graph showing exemplary absorption spectra related to the analysis of the $D_2O$ blank in FIG. 3.

The addition of deuterium oxide ($D_2O$) to the extraction solvent as part of the $D_2O$ blank results in H-D exchange with the water present in the extraction solvent by the following reaction:

$$x \text{ mol } H_2O + y \text{ mol } D_2O \text{ (excess)} \rightarrow x \text{ mol } HOD + (y-x) \text{ mol } D_2O \qquad [6]$$

The spectral outcome of this reaction is illustrated in FIG. 6, where the differential spectrum $CH_3CN—(CH_3CN+D_2O)$ is obtained by subtracting the spectrum DB of the $D_2O$ blank from the corresponding spectrum A of the extraction solvent blank. Because the H-D exchange reaction removes water's HOH bending absorption from the reference spectrum (the spectrum DB of the $D_2O$ Blank), the differential spectrum in FIG. 6 shows a positive absorption directly proportional to the moisture content of the extraction solvent. The absorption bands characteristic of the extract solvent itself, being common to both spectra, are eliminated in the differential spectrum. This procedure is highly specific for water, having a sensitivity of better than 5 ppm with acetonitrile, with the possibility of significantly better sensitivity if sulfolane is used as the extraction solvent. As such, this procedure can be used to determine quite an exact measure of the moisture content of acetonitrile or other aprotic extraction solvent and is a useful quality control tool to ensure that the solvent is suitable for the task of extracting moisture from hydrophobic fluid matrices.

Advantageously, the methodology of the present invention utilizes deuterium oxide ($D_2O$), which via hydrogen-deuterium (H-D) exchange with water provides a means by which to spectrally determine the absolute moisture content of the solvent used for extraction and of the extract-samples to a very high degree of accuracy. The method is also based on differential spectroscopy whereby a reference spectrum is subtracted from the spectrum of the extraction solvent or the spectrum of an extract-sample to produce a differential spectrum which removes the spectral contributions of all constituents common to the two spectra. The selection of the reference spectrum to be employed is dependent on desired accuracy and the analytical objective. For determination of the moisture content of the dry extraction solvent, the reference spectrum employed is the spectrum of an aliquot of the extraction solvent that has been treated with $D_2O$. For determination of the moisture content of extract-samples, the following are the most common alternatives: (a) a split-sample or duplicate analysis technique is used where the reference spectrum is the spectrum of an aliquot of the extract-sample that has been treated with $D_2O$, (b) the spectrum of the extract of a representative pre-dried reference sample of a particular sample type is used as the reference spectrum, in which case the unit moisture content of said extract is determined by the preparation of a sample blank and the value obtained is subtracted from the unit moisture content determined for the extract-sample or (c) the spectrum of the acetonitrile used to prepare the samples is used as the reference spectrum. In addition, the methodology involves the spectroscopic determination of a dilution correction factor, which compensates for any partial miscibility of the sample with the extraction solvent, and the transformation of absorbance spectra to second-derivative spectra through the use of a 5-5 gap-segment algorithm to minimize spectral interferences and baseline issues.

There have been described and illustrated herein several embodiments of a system and a method of determining moisture content in hydrophobic fluid such as lubricants, edible oils, and fuels using an aprotic solvent for extraction of water from the hydrophobic fluid. It also utilizes $D_2O$ to characterize moisture content of the extraction solvent, and compensate for both moisture content of the extraction solvent and matrix effects stemming from miscibility of the hydrophobic fluid in the extraction solvent. While particular embodiments of the invention have been described, it is not intended that the invention be limited thereto, as it is intended that the invention be as broad in scope as the art will allow and that the specification be read likewise. Thus, while particular instruments and apparatuses have been disclosed, it will be appreciated that other instruments and apparatuses may be used as well, including various types of computers, spectroscopic analyzers, and manual or automated systems to conduct sample testing to control and/or monitor the quality of a fluid. In addition, while particular quantities and volumes of reagents and samples have been disclosed, it will be appreciated that other quantities and volumes of reagents and samples may be used. While particular method steps for procuring and testing samples have been disclosed, it will be appreciated that certain steps may be omitted from the method, and/or that other steps may be included in the method. Further, while a particular calibration process has been disclosed, it will be appreciated that other calibration processes and empirical modules relating measured absorbance changes in the IR wavelengths related to moisture may be utilized. While particular attributes of a sample have been measured and particular equations and calculations have been disclosed based on the measured attributes of the sample for calculating specific parameters of the sample, it will be appreciated that other equations may be utilized, other attributes may be measured, and other parameters may be calculated. While the calculation/generation of moisture data has been disclosed which represents or corresponds to the moisture/water components present, it will be appreciated that other moisture data may be calculated and that other methods, protocols, empirical models, and calculations may be employed to determine moisture data and moisture content. It will therefore be appreciated by those skilled in the art that yet other modifications could be made to the provided invention without deviating from its spirit and scope as claimed.

What is claimed is:

1. A method of characterizing water content of a hydrophobic fluid sample, comprising:
    i) providing an aprotic solvent;
    ii) mixing the solvent of i) with water to produce a number of solvent-water mixtures with predetermined water concentrations;
    iii) performing infrared spectroscopic testing of the number of solvent-water mixtures to derive spectrum data for the number of solvent-water mixtures;
    iv) processing the spectrum data for the number of solvent-water mixtures to solve for a calibration equation that relates a spectral property measurable at a predetermined wavelength to unit moisture concentration, wherein the predefined wavelength is in the range between $1615 cm^{-1}$ and $1645 cm^{-1}$;
    v) preparing a mixture by adding the aprotic solvent of i) with at least a portion of the hydrophobic fluid sample whereby the aprotic solvent reacts with the sample to extract water from the sample of the mixture;

vi) performing infrared spectroscopic testing of the mixture of v) to derive spectrum data for the mixture;

vii) processing the spectrum data for the mixture as generated in vi) to measure the spectral property of the calibration equation of iv);

viii) using the measure of the spectral property of vii) as input to the calibration equation derived in iv) in order to output a measure of unit moisture concentration for the mixture of v); and ix) deriving a measure of moisture content of the hydrophobic fluid sample based upon the unit moisture concentration for the mixture as derived in viii).

2. A method according to claim 1, further comprising:

x) splitting the mixture of v), or preparing a duplicate of the mixture of v) to generate a resultant mixture;

xi) mixing the mixture of x) and $D_2O$ to produce a sample blank;

xii) performing infrared spectroscopic testing of the sample blank to derive spectrum data for the sample blank;

xiii) processing the spectrum data for the sample blank of xii) and the spectrum data for the mixture of vi) to derive differential spectrum data;

xiv) processing the differential spectrum data of xiii) to measure the spectral property of the calibration equation of iv); and xv) using the measure of the spectral property of xiv) as input to the calibration equation derived in iv) in order to output a measure of unit moisture concentration; and wherein the calculation of the moisture content of the hydrophobic fluid sample in ix) is based upon the moisture concentration of xv).

3. A method according to claim 1, wherein:

unit moisture concentration of the calibration equation is universal in that it is independent of the sample weight or extraction solvent volume used in the analysis of samples.

4. A method according to claim 1, wherein:

in iv), the calibration equation is derived by fitting spectral properties relating to a predefined wavelength for the number of solvent-water mixtures of ii), wherein the predefined wavelength is at or near $1633 cm^{-1}$.

5. A method according to claim 1, wherein:

the aprotic solvent of i) is selected from the group consisting of acetonitrile, dimethyl sulfoxide, and sulfolane.

6. A method according to claim 1, wherein:

the hydrophobic fluid sample is selected from the group consisting of a lubricant, an edible oil, and a fuel.

7. A method according to claim 1, wherein:

the hydrophobic fluid sample is a lubricant.

8. A method according to claim 1, further comprising:

x) storing the measure of moisture content of the hydrophobic fluid sample as calculated in ix) for output.

9. A method according to claim 8, further comprising:

xi) outputting to a user the measure of moisture content of the hydrophobic fluid sample stored in x).

10. A method according to claim 1, wherein:

the unit moisture content of viii) is defined in micrograms of water per gram of solvent.

11. A method according to claim 10, wherein:

the moisture content of the hydrophobic fluid sample of ix) is defined in ppm.

12. A method according to claim 10, wherein:

the calculating of ix) multiplies the unit moisture concentration of viii) by the ratio of the weight of solvent mixed with the hydrophobic fluid in v) to the weight of the hydrophobic fluid sample mixed with the solvent in v).

13. A method according to claim 1, further comprising:

x) mixing the aprotic solvent of i) and $D_2O$ to produce a $D_2O$ blank;

xi) performing infrared spectroscopic testing of the $D_2O$ blank to derive spectrum data for the $D_2O$ blank;

xii) processing the spectrum data for the $D_2O$ blank of xi) and spectrum data for the aprotic solvent of i) to derive differential spectrum data;

xiii) processing the differential spectrum data of xii) to measure the spectral property of the calibration equation of iv); and xiv) using the measure of the spectral property of xiii) as input to the calibration equation derived in iv) in order to output a measure of unit moisture concentration for the aprotic solvent of i).

14. A method according to claim 13, wherein:

the calculation of the moisture content of the hydrophobic fluid sample in ix) is based upon the unit moisture concentration of xiv).

15. A method according to claim 13, further comprising:

xv) using the unit moisture concentration of xiv) to evaluate the dryness of the solvent of i).

16. A method according to claim 1, wherein:

the processing of iv) includes the derivation of differential spectrum data for the number of solvent-water mixtures of ii), and processing the differential spectrum data for the number of solvent-water mixtures of ii) to derive final spectrum data for the number of solvent-water mixtures of ii); and the processing of vii) includes the derivation of differential spectrum data for the extract-sample, and processing the differential spectrum data for the mixture of v) to derive final spectrum data for the mixture of v).

17. A method according to claim 16, wherein:

the differential spectrum data of iv) and vii) are based on a 5-5 (gap-segment) derivative of spectral data.

18. A method according to claim 16, wherein:

in iv), the calibration equation is derived by fitting spectral properties measured at the predetermined wavelength of the final spectrum data for the number of solvent-water mixtures of ii) to measures of unit moisture concentration for the number of solvent-water mixtures of ii);

in vii), a spectral property is measured at the predetermined wavelength of the final spectrum data for the extract-sample; and in viii), the spectral property measured in vii) is input to the calibration equation derived in iv).

19. A method according to claim 16, wherein:

the differential spectrum data of iv) and vii) are based on respective correction factors derived from spectral data at or near $2070 cm^{-1}$.

20. A method according to claim 19, wherein:

the respective correction factors are further based on first spectral data at or near $2080 cm^{-1}$ and second spectral data at or near $2040 cm^{-1}$.

\* \* \* \* \*